United States Patent [19]

Yeh

[11] Patent Number: 5,387,675

[45] Date of Patent: Feb. 7, 1995

[54] MODIFIED HYDROPHOBIC CATIONIC THICKENING COMPOSITIONS

[75] Inventor: Michael H. Yeh, Hamilton, N.J.

[73] Assignee: Rhone-Poulenc Specialty Chemicals Co., Cranbury, N.J.

[21] Appl. No.: 29,208

[22] Filed: Mar. 10, 1993

[51] Int. Cl.⁶ .................. C07H 5/04; C07H 5/06; C08B 37/00

[52] U.S. Cl. .................. 536/18.7; 536/22.1; 536/50; 536/52; 536/114; 536/120

[58] Field of Search .......... 536/18.7, 22.1, 50, 536/52, 120, 114

[56] References Cited

U.S. PATENT DOCUMENTS

| | | | |
|---|---|---|---|
| 3,467,647 | 9/1969 | Benninga | 260/209 |
| 3,760,881 | 9/1973 | Kiel | 166/308 |
| 3,833,527 | 9/1974 | Puikkinen et al. | 260/9 |
| 4,031,307 | 6/1977 | DeMartino et al. | 536/114 |
| 4,264,322 | 4/1981 | Lewis et al. | 8/479 |
| 4,276,414 | 6/1981 | Tessler | 536/114 |
| 4,403,360 | 9/1983 | Finney et al. | 8/151 |
| 4,454,617 | 6/1984 | Moates et al. | 8/151 |
| 4,568,481 | 2/1986 | Harris, Jr. | 252/8.55 R |
| 4,758,282 | 7/1988 | Stober et al. | 127/34 |
| 4,918,181 | 4/1990 | Karcher et al. | 536/114 |
| 4,959,464 | 9/1990 | Yeh | 536/114 |
| 5,186,928 | 2/1993 | Birtwistle | 424/70 |
| 5,227,481 | 7/1993 | Tsai et al. | 536/18.7 |
| 5,233,032 | 8/1993 | Zody et al. | 536/114 |

FOREIGN PATENT DOCUMENTS

0405664 1/1991 European Pat. Off. .

Primary Examiner—Ronald W. Griffin
Attorney, Agent, or Firm—Andrew M. Solomon

[57] ABSTRACT

Water soluble quaternary ammonium ethers of polysaccharides or polyols wherein the quaternary ammonium ether substituents correspond to the formula

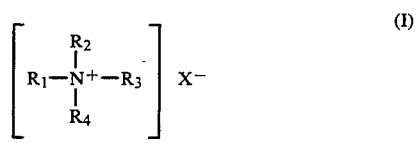

(I)

wherein $R_1$ is a monohydroxylated or polyhydroxylated alkyl group containing between about one and about six carbon atoms; $R_2$ and $R_3$ are independently, alkyl groups containing between about one and about six carbon atoms; $R_4$ is an alkyl group containing between about six and about 24 carbon atoms; and X is a halide, wherein the degree of substitution of said ethers ranges from about 0.001 to about 0.5. is provided. The composition have multiple uses as thickeners and are particularly suited for use in personal care products.

12 Claims, No Drawings

MODIFIED HYDROPHOBIC CATIONIC THICKENING COMPOSITIONS

BACKGROUND OF THE INVENTION

1. Field of the Invention

The present invention relates to a cationic thickening composition. More specifically, the composition is a polysaccharide or polyol which is reacted with a hydroxylated quaternary ammonium halide wherein the quaternary ammonium halide contains a long chain aliphatic group containing at least 6 carbon atoms. The resulting compositions function to increase the viscosity of an aqueous solution and have widespread uses, for example, in cosmetics and in oil recovery.

2. Technology Description

Natural and synthetic polymers containing hydroxy groups have been used as thickeners for foods, coatings, paints, explosive slurries, oil well fluids, cosmetics and other personal care products, and many other functional applications.

One class of polymers that have been widely used as suspending and viscosity agents are polygalactomannans. Polygalactomannans are polysaccharides composed principally of galactose and mannose units and are usually found in the endosperm of leguminous seeds such as guar, locust bean, honey locust, flame tree, and the like. The polygalactomannans may be used in either their natural form or may be substituted with one or more functional groups (e.g., carboxymethyl group). In practice, to thicken a fluid the polygalactomannans may either be added by themselves, or with other viscosity modifiers such as other polygalactomannans, xanthan gum and the like.

Other polymers proposed for use as thickening agents include unmodified and modified starches, methyl cellulose, hydroxyethyl cellulose, carboxymethyl cellulose, polyols such as polyvinyl alcohol, glycols, glycerols, polyacrylamide, polyvinylpyrrolidone, xanthan gum and the like.

U.S. Pat. No. 3,467,647 discloses polysaccharides containing both cationic and anionic substituents. Amongst the starting polysaccharides which are then modified according to this patent include starches, locust bean gum (carob gum) and guar gum. Suggested cationic substituents include primary, secondary or tertiary amino groups, quaternary ammonium, sulphonium or phospinium groups. The reference suggests that cationic groups may be introduced into the polysaccharide molecule by reacting the polysaccharide with any of the following reagents: ethylene imine, N-(2-hydroxyethyl) ethylene imine, cyanamide, beta morpholinoethylchloride, beta diethyl aminoethylchloride, 3-diethyl amino 1,2-epoxypropane dimethyl aminoethyl methacrylate, N-(2,3-epoxypropyl) trimethyl ammonium chloride, (4-chlorobutene-2)-trimethyl ammonium chloride, 2-chloroethyl methyl ethyl sulphonium iodide and 2-chloroethyl tributylphosphonium chloride.

U.S. Pat. No. 3,760,881 discloses well treating fluids which are prepared with complexes formed by the reaction of aliphatic quaternary ammonium compounds with water-soluble compounds such as monosaccharides, disaccharides, trisaccharides, polysaccharides, and long chain synthetic hydroxylated polymers, such as polygalactomannans. Preferred quaternary substituents include trimethyl alkyl ammonium chlorides, wherein alkyl represents a long chain alkyl group having between about 6 and about 18 carbon atoms. The reference does not disclose nor suggest that the quaternary ammonium halide be hydroxylated. A preferred polygalactomannan mentioned is guar gum.

U.S. Pat. No. 3,833,527 discloses a water soluble hemicellulose material made soluble by the reaction of a hemicellulose with an adduct comprising 3-chloro-2-hydroxypropyltrimethylammonium chloride or glycidyltrimethylammonium chloride. The hemicellulose is made water soluble to effect its disposal from waste effluent streams of pulp mills.

U.S. Pat. No. 4,031,307 discloses cationic polygalactomannan compositions. The compositions are prepared by reacting a polygalactomannan with a quaternary ammonium halide compound. The reactant quaternary ammonium halide compound contains three alkyl groups containing between one and six carbon atoms and one alkenyl group containing between one and six carbon atoms. An example of one such reactant is 4-chloro-2-butenyl trimethylammonium chloride. The degree of substitution on the polygalactomannan compound ranges between 0.05 and 2.5.

U.S. Pat. Nos. 4,264,322; 4,403,360 and 4,454,617 disclose dye compositions for textile fibers. The compositions comprise an admixture of immiscible gel phases, wherein one gel phase is thickened with a cationic gelling agent and wherein a second gel phase, which is dispersed in the first gel phase, is thickened with an anionic gelling agent. Suggested cationic gelling agents for the first phase include cationic polygalactomannans containing quaternary ammonium groups. Specific examples of such cationic reactants include 2,3-epoxypropyltrimethylammonium chloride, hydroxypropyltrimethylammonium chloride, tetramethylammonium chloride and bromide, benzyltrimethylammonium chloride and bromide, tetraethylammonium chloride and bromide, tetrabutylammonium chloride and bromide, methylpyridinium chloride and bromide, benzylpyridinium chloride and bromide, trimethyl-p-chlorobenzylammonium chloride and bromide, and triethanolmethylammonium chloride and bromide.

U.S. Pat. No. 4,758,282 discloses a dry process for the production of cationic galactomannans by reaction of the galactomannan starting material with an alkylidene epoxide in the presence of water and in the presence of finely divided hydrophilic silicic acid. The preferred alkylidene epoxide is 2,3-epoxypropyltrimethylammonium chloride. The reference further discloses that the reaction between the galactomannan and the epoxide be carried out in the presence of 0.5 to 5% of 2,3-epoxypropyldodecyldimethylammonium acetate.

U.S. Pat. No. 4,959,464 discloses derivatized polygalactomannan compounds. The compounds are prepared by reacting a polygalactomannan with a derivatizing agent, followed by the addition of an aluminum salt to crosslink the surface of the resulting compound. One class of derivatizing agents disclosed is quaternary ammonium alkylating agents. Specific examples of such agents are 2,3-epoxypropyl trimethylammonium chloride and 3-chloro-2-hydroxypropyl trimethyl ammonium chloride.

EP 0 405 664 discloses personal care compositions, and specifically liquid and solid soap compositions containing a cationic polymer which has a non-labile bulky amine moiety. Specific examples of preferred bulky amine polymers include the following:

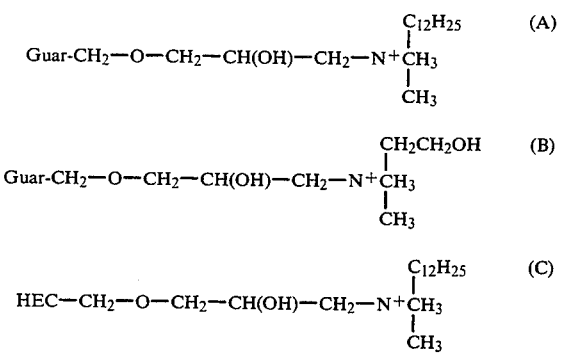

These polymers have a degree of substitution reported to be ranging from about 0.5 to about 4, preferably between 1 and 2.5 and are used to replace comparable quaternary polymers which do not contain the bulky amine moiety and are alleged to be malodorous. As these levels of substitution it is nearly impossible to manufacture the molecules, and where possible, the molecules are extremely expensive to manufacture.

Despite the above, there still is a need for compositions which demonstrate enhanced viscosity behavior.

BRIEF SUMMARY OF THE INVENTION

In accordance with the present invention, novel water soluble cationic viscosity increasing compositions are provided. The compositions provide enhanced viscosities when added in solution and provides both cationic and hydrophobic properties. They also can provide a synergistic increase in viscosity when combined with one or more anionic viscosity increasing compositions and can also interact with surfactants and salts to enhance viscosity and in some cases form a cross-linked gel. The novel composition comprises a polysaccharide or polyol which is reacted with a hydroxylated quaternary ammonium halide wherein the quaternary ammonium halide contains a long chain aliphatic group containing at least 6 carbon atoms.

In accordance with a preferred embodiment, the present invention comprises water soluble quaternary ammonium ethers of polysaccharides or polyols wherein the quaternary ammonium ether substituents correspond to the formula

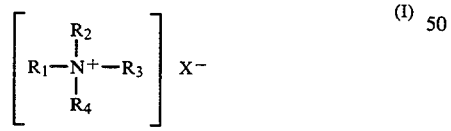

wherein $R_1$ is a monohydroxylated or polyhydroxylated alkyl group containing between about one and about six carbon atoms; $R_2$ and $R_3$ are independently, alkyl groups containing between about one and about six carbon atoms; $R_4$ is an alkyl group containing between about six and about 24 carbon atoms; and X is a halide. In particularly preferred embodiments, the polymers comprise polygalactomannans derived from guar gum or locust bean gum, and preferably guar gum. Further, the preferred degree of substitution of the quaternary ammonium groups onto the polymer is between about 0.001 and about 0.5. In addition, $R_1$ preferably comprises a 2-hydroxypropyl group and $R_4$ comprises an alkyl group having between 10 and 21 carbon atoms.

The compositions are particularly effective as thickening agents. They may be used for a number of functional applications such as in textiles, paper products, explosives, oil field chemicals, agricultural applications, personal care products, cosmetics and the like.

It has been difficult in the past to provide water soluble materials containing long chain alkyl groups. The presence of the cationic groups allows the present materials to be both hydrophobic and water soluble. As a result these materials may be used in a number of applications which are water based, such as personal care products, which are ultimately less expensive to make as water is the primary solvent utilized.

Another embodiment of the present invention comprises a process for producing a viscous liquid or a gel. The process comprises the step of adding to a solvent, preferably water, 0.5 parts to about 2.0 parts per 100 parts viscous liquid or gel of the above defined cationic polymer. A further embodiment comprises provided a highly cross-linked gel by adding known cross-linking agents to the solvent.

A third embodiment of the present invention comprises a textile, paper product, explosive, oil field chemical, agricultural chemical, personal care product or cosmetic including an amount of the above-defined cationic polymer.

Accordingly, it is an object of the present invention to provide a novel composition which can increase the viscosity of a liquid and, when combined with other viscosity modifiers, demonstrates a superior viscosity profile as compared to the materials individually.

It is another object of the present invention to provide a process for producing a viscous liquid or gel using a novel composition.

A further object of the present invention to provide a paper product, explosive, oil field chemical, agricultural chemical, textile, personal care product or cosmetic which includes a novel thickener composition.

These, and other objects, will readily be apparent to those skilled in the art as reference is made to the detailed description of the preferred embodiment.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

The present invention comprises water soluble quaternary ammonium ethers of polysaccharides or polyols wherein the quaternary ammonium ether substituents correspond to the formula

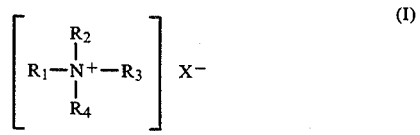

wherein $R_1$ is a monohydroxylated or polyhydroxylated alkyl group containing between about one and about six carbon atoms; $R_2$ and $R_3$ are independently, alkyl groups containing between about one and about six carbon atoms; $R_4$ is an alkyl group containing between about six and about 24 carbon atoms; and X is a halide, the degree of substitution of said polysaccharide or polyol ranging from about 0.001 to 0.5.

A number of materials can be used as the starting polysaccharide or polyol. Particularly preferred are polygalactomannans. Polygalactomannans are polysaccharides composed principally of galactose and mannose units and are usually found in the endosperm of leguminous seeds, such as guar, locust bean, honey locust, flame tree, and the like. Guar flour, for example, is composed mostly of a galactomannan which is essentially a straight chain mannan with single membered galactose branches. The mannose units are linked in a 1-4-β-glycosidic linkage and the galactose branching takes place by means of a 1-6 linkage on alternate mannose units. The ratio of galactose to mannose in the guar polymer is, therefore, one to two. Guar gum has a molecular weight of about 1.5 million daltons.

Locust bean gum is also a polygalactomannan gum of similar molecular structure in which the ratio of galactose to mannose is one to four. Guar and locust bean gum are the preferred sources of the polygalactomannans, principally because of the commercial availability thereof.

In use the polygalactomannan may be either in its natural state (i.e., pure guar gum or locust bean gum) or may be derivatized. Derivatized polygalactomannans include one or more non-ionic groups. Examples of such polygalactomannans include hydroxypropyl guar, hydroxyethyl guar, and the like. Such derivatized polygalactomannans are sold by Rhône-Poulenc Inc. under the trade names Jaguar 8012, Jaguar 8060, Jaguar 8000, Jaguar HP-20 and Jaguar HP-23.

Alternative materials which may be selected as the starting material include starches, celluloses, xanthan gum, alginates and polyols. Examples of starches include both natural and modified starches, such as dextrinated, hydrolyzed, oxidized, cross-linked, alkylated, hydroxyalkylated, acetylated, or fractionated (e.g., amylose and amylopectin). The starch may be of any origin, for example, corn starch, wheat starch, potato starch, tapioca starch, sago starch, rice starch, waxy corn starch or high-amylose corn starch.

Examples of celluloses include hydroxyethyl cellulose, hydroxypropyl cellulose, and alkyl celluloses.

Examples of alginates include starch alginate.

Examples of polyols include polyvinyl alcohol, polyethylene glycol and glycerol.

When the starting material selected is a polygalactomannan, it is preferred that the degree of substitution ranges from about 0.001 to about 0.5. By the term "degree of substitution" as employed herein is meant the average substitution of cationic or anionic groups per anhydro sugar unit in the polysaccharides, and particularly, polygalactomannan gums. In guar gum, the basic unit of the polymer consists of two mannose units with a glycosidic linkage and a galactose unit attached to the 6-hydroxyl group of one of the mannose units. On the average, each of the anhydro sugar units contains three available hydroxyl sites. A degree of substitution of three would mean that all of the available hydroxyl sites have been esterified with formate ester groups.

Particularly preferred embodiments of the present invention comprise cationic polygalactomannans having a degree of substitution of about 0.01 to about 0.50 more preferred embodiments have a degree of substitution of about 0.01 to about 0.40, and most preferred embodiments comprise cationic polygalactomannans having a degree of substitution of about 0.02 to about 0.20.

The cationic nature is obtained by utilizing a substituent of formula (II)

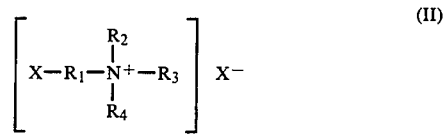

(II)

wherein $R_1$, $R_2$, $R_3$, $R_4$, and X are as defined above. Particularly preferred monomers include those wherein $R_1$ preferably comprises a 2-hydroxypropyl group, $R_2$ and $R_3$ comprise methyl groups, $R_4$ comprises an alkyl group having between 10 and 21 carbon atoms and X comprises chloride. Examples of such monomers include 3-chloro-2-hydroxypropyl N,N,N-dodecyldimethylammoniumchloride, 3-chloro-2-hydroxypropyl N,N,N-cocoalkyldimethylammonium chloride, and 3-chloro-2-hydroxypropyl N,N,N-octadecyldimethylammonium chloride. Such chemicals are commercially available from The Degussa Chemical Company under the trade names QUAB-342, QUAB-360 and QUAB-426.

The cationic derivatives of the polymers, and particularly guar gum or locust bean gum are prepared by contacting solid guar gum or locust bean gum with the above-defined haloalkyl-substituted quaternary ammonium compound and a stoichiometric excess of alkali metal hydroxide or ammonium hydroxide in a reaction medium comprising an aqueous solution of water-miscible solvent, at a temperature between about 10° C. and about 100° C. for a reaction period sufficient to achieve a desired degree of substitution.

The solid guar gum or other polygalactomannan which is etherified can be in the form of endosperm splits or in the form of finely divided powder which is derived from the endosperm splits. It is important that the polygalactomannan gum being etherified with quaternary ammonium groups remains as a solid phase in the reaction medium during the reaction period.

Further details on the synthesis of cationic quaternary ammonium type polymers are provided in U.S. Pat. No. 4,031,307. To the extent necessary, this patent is incorporated by reference.

In use, the inventive compositions can effectively function as thickeners when added to a solvent, typically water. This typically comprises adding between about 0.5 and about 2.0 parts of the cationic polymer per 100 parts of viscous liquid or gel. While the viscosity profile obtained by using the cationic polymers alone is adequate, results can be synergistically enhanced when using the cationic polymers in solution in combination with anionic polymers in solution to produce an amphoteric blend composition. While less preferred, the anionic and cationic polymers can be first mixed together in solid form and then added as a blend composition in a solvent.

Such amphoteric polygalactomannan blend compositions are typically produced by combining solutions of both cationic and anionic polymers in respective amounts so that the positive and negative charges are equally balanced. The respective amounts of anionic and cationic solutions are added together based primarily upon the degree of substitution of each. For example, larger amounts of a low degree of substitution cationic polymer solution may be added to smaller amounts of a high degree of substitution anionic solution.

While in the preffered embodiment, the amounts of anionic and cationic solutions are added to produce a charge neutral solution, the amounts of each may be varied to yield solutions which have an overall positive or negative charge. Although not as enhanced as when producing a charge neutral solution, some synergistic effect is achieved by unbalanced charged additions.

For easy handling and ready dispersibility, the gums should have a particle size of less then about 100 mesh. Other components, e.g., fillers, wetting agents, dispersants, bactericides, fungicides and the like can be mixed with the powdered blends of the invention if so desired.

It is believed that the viscosity and/or firmness of the gel increases with increasing amounts of blend composition added. At lower levels the gels are pumpable viscous liquids. Increasing the amount of blend composition can yield a firm, cohesive gel.

The novel cationic polymers have a wide number of possible uses. Amongst them are as suspending agents for various solids, such as in oil field chemicals, for use in textiles, for use in paper products, for use in cosmetics and other personal care products, for use with agricultural products, for use is explosives, and the like. Other uses will readily be appreciated by those skilled in the art.

A feature of the inventive cationic polymers is their affinity towards water. In general, long chain aliphatic hydrocarbon compounds do not have an affinity to water, making the reaction with polymers such as polygalactomannans difficult to achieve. The inventors have discovered that if reagents of formula (II) are used, the reaction conditions are improved. In this class of reagents the long chain alkyl group is linked on the nitrogen atom to form an ammonium salt and is water soluble. As a result, it is believed that the inventive materials are ideally suited for use in aqueous based personal care products such as cosmetics, lotions, and the like.

The invention is described in greater detail by the following non-limiting examples.

EXAMPLE 1

2000 parts of oxidized guar gum are slurried in 80% isopropanol. 50 parts of 50% NaOH are added and the mixture is stirred for 30 minutes. 380 parts of QUAB-342, 3-chloro-2-hydroxypropyl N,N,N-dodecyldimethylammonium chloride, are added and the etherification reaction is conducted at 70°–80° C. over a period of about one to six hours. The reaction mixture is neutralized to a pH of about 7 with acetic acid, washed with isopropanol, recovered and air dried. The degree of substitution for this material is about 0.01.

A 2% aqueous solution of this compound in water is prepared by adding 2 parts of this composition to 98 parts of water. The viscosity determined by a Brookfield RTV Viscometer at 20 rpm is above 4000 cps.

EXAMPLE 2

100 parts of a 40% solution of QUAB-342, 40 parts water and 3 drops of concentrated HCl are mixed together and added to 267 parts of Jaguar 8012, a guar gum manufactured by Rhône-Poulenc Inc. The mixture is mixed at room temperature for about 20 to 30 minutes. 19 parts of a 50% NaOH solution is sprayed onto the solution, the mixture is mixed at room temperature for about 20 to 30 minutes and the mixture is then heated in a closed container at about 70°–80° C. for about two to three hours. The mass is cooled to room temperature and is sprayed with a solution of 7.2 grams acetic acid and 11 ml of water. The mixture is washed twice with acetone and dried in an oven. The viscosity of a 1% aqueous solution of this material is 150 cps. The viscosity of a 2% aqueous solution of this material is 2600 cps. The viscosity of a 1% solution of this material in methanol is 300 cps. The viscosity of a 2% solution of this material in methanol is 3150 cps.

To demonstrate the enhanced viscosity effects when combining this material with an anionic material, one gram of this material is added to 179 ml of water. The viscosity profile of this solution is shown below under Sample A. 15 grams of an ammonium lauryl sulfate solution and 3 grams of NH$_4$Cl are added to the solution. The viscosity profile of this solution is shown below under Sample B. 20 grams of an ammonium lauryl sulfate solution and 3 grams of NH$_4$Cl are added to the initial solution. The viscosity profile of this solution is shown below under Sample C. 20 grams of an ammonium lauryl sulfate solution and 4 grams of NH$_4$Cl are added to the initial solution. The viscosity profile of this solution is shown below under Sample D.

| Viscosity Profile of Example 2 Material (cps) | | | | |
| --- | --- | --- | --- | --- |
| LVT RPM | Sample A | Sample B | Sample C | Sample D |
| .3 | — | — | 500 | 1800 |
| .6 | — | — | 300 | 1300 |
| 1.5 | 80 | — | 216 | 1040 |
| 3.0 | 90 | 100 | 160 | 940 |
| 6.0 | 85 | 95 | 140 | 900 |
| 12 | 80 | 92.5 | 130 | 975 |
| 30 | 72 | 96 | 126 | 935 |
| 60 | 65 | — | — | 890 |

Qualitatively, Sample B is slightly thicker than Sample A but still watery. Sample C becomes a viscous, associated solution, and Sample D becomes a cross-linked gel which is very soft and elastic. It is further attempted to replicate the experiment by first adding the ammonium lauryl sulfate solution to the water and then adding the material of Example 2. Using this addition sequence, the solution does not thicken.

EXAMPLE 3

The synthesis procedure of Example 2 is repeated except that the acetone washing step is omitted. The viscosity of a 1% aqueous solution of this material is 60 cps. The viscosity of a 2% aqueous solution of this material is 360 cps. The viscosity of a 1% solution of this material in methanol is 150 cps. The viscosity of a 2% solution of this material in methanol is 1700 cps.

To demonstrate the enhanced viscosity effects when combining this material with an anionic material, one gram of this material is added to 179 ml of water. The viscosity profile of this solution is shown below under Sample A. 15 grams of an ammonium lauryl sulfate solution and 2 grams of NH$_4$Cl are added to the solution. The viscosity profile of this solution is shown below under Sample B. 15 grams of an ammonium lauryl sulfate solution and 3 grams of NH$_4$Cl are added to the initial solution. The viscosity profile of this solution is shown below under Sample C. 20 grams of an ammonium lauryl sulfate solution and 3 grams of NH$_4$Cl are added to the initial solution. The viscosity profile of this solution is shown below under Sample D. 20 grams of an ammonium lauryl sulfate solution and 4 grams of NH4Cl are added to the initial solution. The viscosity profile of this solution is shown below under Sample E.

| | Viscosity Profile of Example 3 Material (cps) | | | | |
|---|---|---|---|---|---|
| LVT RPM | Sample A | Sample B | Sample C | Sample D | Sample E |
| .6 | 50 | 200 | 1250 | 2100 | — |
| 1.5 | 64 | 152 | 1100 | 1920 | 8000 |
| 3.0 | 60 | 138 | 920 | 1720 | 8000 |
| 6.0 | 52 | 125 | 875 | 1700 | 7600 |
| 12 | 52 | 122.5 | 850 | 1500 | 6300 |
| 30 | 50 | 127 | 890 | 1440 | 5100 |
| 60 | 48.5 | 120 | 890 | 1290 | 4500 |

COMPARATIVE EXAMPLE 4

The testing of Examples 3 and 4 is repeated except that the cationic polymer is replaced by Quatrisoft Polymer LM-200, a commercially available cationic polymer manufactured by Amechol Corp. The polymer will initially associate with small amounts (0.25%) of the ammonium lauryl sulfate solution to provide enhanced viscosities, but once the amounts of the ammonium lauryl sulfate solution are increased (0.50% or above), the viscosity decreases. Further, once any amount of salt such as NH4Cl is added, the LM-200 "salts out" such that the polymer floats to the top of the solution.

COMPARATIVE EXAMPLE 5

The testing of Examples 3 and 4 is repeated except that the cationic polymer is replaced by Jaguar 8012, a commercially available non-ionic polymer that does not have a long chain alkyl group. For all additions of ammonium lauryl sulfate and NH4Cl added, the viscosities are lower than those obtained when producing solutions of the Jaguar 8012 alone.

EXAMPLE 6

1000 parts of oxidized guar gum are slurried in 1000 parts of isopropanol. 120 parts of NaOH are added and the mixture is stirred for about 20-30 minutes. 1050 parts of QUAB-342, 3-chloro-2-hydroxypropyl dimethyl dodecyl ammonium chloride, are added and the etherification reaction is conducted at 65° C. over a period of 1.5 to 6 hours. After cooling, the reaction product is washed with acetone to remove the excess reagent and cationic byproducts. The degree of substitution for this material is about 0.055. A 2% aqueous solution of this compound in water is prepared by adding 2 parts of this composition to 98 parts of water. The viscosity determined by a Brookfield RTV Viscometer at 20 rpm is 1550 cps.

EXAMPLE 7

1000 parts of oxidized guar gum are slurried in 1000 parts of isopropanol. 120 parts of NaOH are added and the mixture is stirred for about 20-30 minutes. 1250 parts of QUAB-360, 3-chloro-2-hydroxypropyl N,N,N-cocoalkyldimethylammonium chloride, are added and the etherification reaction is conducted at 65° C. over a period of 1.5 to 6 hours. After cooling, the reaction product is washed with acetone to remove the excess reagent and cationic byproducts. The degree of substitution for this material is about 0.031.

A 2% aqueous solution of this compound in water is prepared by adding 2 parts of this composition to 98 parts of water. The viscosity determined by a Brookfield RTV Viscometer at 20 rpm is 1875 cps.

Having described the invention in detail and by reference to the preferred embodiments thereof, it will be apparent that modifications and variations are possible without departing from the scope of the appended claims.

What is claimed is:

1. Water soluble quaternary ammonium ethers of polysaccharides or polyols wherein the quaternary ammonium ether substituents correspond to the formula

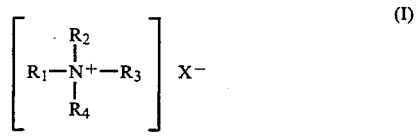

wherein $R_1$ is a monohydroxylated or polyhydroxylated alkyl group containing between one and about six carbon atoms; $R_2$ and $R_3$ are independently, alkyl groups containing between one and about six carbon atoms; $R_4$ is an alkyl group containing between about six and about 24 carbon atoms; and X is a halide, wherein the degree of substitution of said ethers ranges from about 0.001 to about 0.5.

2. The composition according to claim 1 wherein said polysaccharide or polyol is selected from the group consisting of polygalactomannans, starches, celluloses, xanthan gum and alginates.

3. The composition according to claim 2 wherein said polysaccharide or polyol comprises a polygalactomannan.

4. The composition according to claim 3 wherein said polygalactomannan comprises a derivatized or underivatized guar gum or locust bean gum.

5. The composition according to claim 4 wherein the degree of substitution of said quaternary ammonium groups is between about 0.01 and about 0.50.

6. The composition according to claim 5 wherein $R_1$ comprises a 2-hydroxypropyl group.

7. The composition according to claim 6 wherein $R_2$ and $R_3$ comprise methyl groups.

8. The composition according to claim 7 wherein $R_4$ comprises an alkyl group having between about 10 and about 21 carbon atoms.

9. The composition according to claim 8 wherein $R_4$ is selected from the group consisting of dodecyl, cocoalkyl and octadecyl groups.

10. The composition according to claim 9 wherein the degree of substitution of said quaternary ammonium groups is between about 0.02 and about 0.50.

11. The composition according to claim 1 wherein X comprises chloride.

12. The composition according to claim 5 which is cross-linked.

* * * * *